(12) United States Patent
Stansbury et al.

(10) Patent No.: US 6,961,072 B2
(45) Date of Patent: Nov. 1, 2005

(54) METHOD AND SYSTEM FOR VIEWING CHROMATOGRAPHIC PEAKS OVER A NETWORK

(75) Inventors: David Stansbury, The Woodlands, TX (US); Yubo Xu, The Woodlands, TX (US); Jiandong Guo, The Colony, TX (US); David Furr, Spring, TX (US)

(73) Assignee: Infologic, Inc., Shenandoah, TX (US)

( * ) Notice: Subject to any disclaimer, the term of this patent is extended or adjusted under 35 U.S.C. 154(b) by 195 days.

(21) Appl. No.: 10/126,378

(22) Filed: Apr. 19, 2002

(65) Prior Publication Data

US 2003/0197717 A1    Oct. 23, 2003

(51) Int. Cl.[7] .......................... G06G 5/00; G06T 11/20
(52) U.S. Cl. ..................................... 345/667; 345/440
(58) Field of Search ............................... 345/667, 668, 345/669, 670, 671; 382/129, 190

(56) References Cited

U.S. PATENT DOCUMENTS

| | | | |
|---|---|---|---|
| 6,025,844 A | | 2/2000 | Parsons |
| 6,035,323 A | * | 3/2000 | Narayen et al. ............ 709/201 |
| 6,052,110 A | | 4/2000 | Sciammarella et al. |
| 6,175,832 B1 | * | 1/2001 | Luzzi et al. .................. 707/10 |
| 6,195,449 B1 | * | 2/2001 | Bogden et al. ............. 382/129 |
| 6,243,865 B1 | * | 6/2001 | Wei et al. ...................... 725/41 |
| 6,260,044 B1 | * | 7/2001 | Nagral et al. ............... 707/102 |

OTHER PUBLICATIONS

Dessy, Ray. "Collect Your Wandering Thoughts". Analytical Chemistry. vol. 71, No. 13, pp. 482 A-483 A, 1999.*
Williams, Dave. "Making Scientific Data an Enduring Asset". BIOPHARM, Mar. 2001.*
Goffredo, Mary Ellen. "Data Management Solutions for the Enterprise". Chemistry in Britain. Mar. 2002.*
Microsoft® Word 2000 (Copyright 1983-1999).*

* cited by examiner

Primary Examiner—Ryan Yang
(74) Attorney, Agent, or Firm—Mary J. Gaskin

(57) ABSTRACT

A method and system of publishing datafile and metafile images over a network connection. A user can use a web page to transmit the name of a datafile to the server hosting the peak viewing program. The server then processes the information, launches Chromview to generate the metafiles, then uses a series of HTML pages to display the information in a .PNG image file of the datafile on the user's computer screen. This page would have the datafile image, as well as information about the datafile (as applicable), such as the list of available ions, and start/stop times. The user could select an ion, or a start/stop time, and the resulting picture for the datafile would be displayed on his screen. The user can enlarge chosen areas of chromatograms and fragmentograms by entering values in text boxes or by clicking on two opposite corners of the selected area. The user can use either remote (Internet) or local (intranet) means to access the datafiles.

19 Claims, 6 Drawing Sheets

METHOD AND SYSTEM FOR VIEWING CHROMATOGRAPHIC PEAKS OVER A NETWORK

FIELD OF THE INVENTION

The present invention relates to a method and system of publishing datafile and metafile images, as well as information relevant to those images, over a network, particularly one using Internet or intranet technology.

BACKGROUND OF THE INVENTION

Chemists and other scientists frequently use analytical laboratory data in the form of chromatograms and fragmentograms generated by gas chromatography (GC) or gas chromatography/mass spectrometry (GC-MS) instruments. Such scientists have a need to view GC and GC-MS data via the Internet from their personal computers. It is known in the art that a GC or GC-MS trace can be converted to web-compatible graphic files such as JPEG or GIF formats. However, in doing so, the trace becomes a static image and loses resolution when zooming or stretching operations are performed. To overcome these drawbacks, programmers have used Java Applets in order to provide interactivity. However, issues related to Internet security have led to the installation of firewalls, most of which prohibit the downloading and execution of Java applications.

SUMMARY OF THE INVENTION

The present invention uses server application technology and JavaScript to allow a user to view GC or GC-MS traces interactively, without downloading or running any application other than the web browser. The method publishes datafile and metafile images and relevant information over a network, using Internet or intranet technology.

In carrying out the present invention, processed data files consisting of analytical results are stored on a server at a location separate from the user; i.e., at an analytical laboratory or other storage facility. A user, such as a geochemist, accesses the data over the Internet, selecting a datafile which references a GC or GC-MS analysis he wishes to view, then transmitting the name of that datafile over a network connection to the server which uses the method of the present invention (hereinafter sometimes called the peak viewing program). The peak viewing program, which is built using Microsoft Active Service Page (ASP) technology, runs on Microsoft Internet Information Server. The chromatogram trace of the requested GC or GC-MS analysis is generated and converted to a picture (i.e., a .PNG file) by Chromview and MetaConverter, which are components running on the server; the picture is sent to the user on a web page for viewing, zooming, and turning on/off various trace attributes. Because the Chromview and MetaConverter components operate on the server, the user does not download or operate any software. The entire operation occurs over a browser window, and it functions within the parameters of normal browser capacity and security. In the present example, the requested datafile could reference a GC-MS analysis, with a variety of ions available for viewing. The list of available ions would appear beside the image, each one acting as a hyperlink which would transmit to the server the name of the datafile and the ion requested. If one of the hyperlinks is clicked, the information goes to the server, generating a new .PNG file matching the selected ion, which appears on the screen, again with the list of available ions.

If the user wishes to enlarge his view of a particular amplitude or time-related start and end points, he can enter the points he would like to "zoom in" on in a side menu box, or he can use the mouse to select the area to be enlarged by two mouse clicks, one at each diagonal corner of a rectangle defining the area. (Under currently available browser technology, zooming is performed by clicking and dragging a rectangle to define the area to be enlarged, the process of which requires an application to be downloaded to the user's computer.) This information is once again sent to the server and processed, and the updated .PNG file is sent back to the browser window for viewing. Since a new image is generated and displayed, no loss of resolution occurs. The entire process takes place on the server, requiring the user to do nothing more than manage the browser window. In the present example, the user can be coupled over a network setting or he can access the server remotely through an Internet connection. In either case, the connection operates using Hypertext Transfer Protocol (HTTP).

The peak viewing program of the present invention can be plugged into any website that wishes to display GC or GC-MS data online. The peak viewing program can read multiple output file formats generated from different vendors. Laboratories that deal with GC and GC-MS data can use the peak viewing program as an internal quality control tool or as a data delivery method. Chemists who deal with GC and GC-MS data can use the peak viewing program as an add-on to their web-based data browser.

It is an object of the present invention to allow a user to view GC and GC-MS data via the Internet through a web browser without having to install local applications.

It is another object of the present invention to allow a user to view GC and GC-MS data via the Internet using only his preferred Internet browser.

Yet another object of the present invention is to allow users all over the world to access data residing in a central data storage location.

Still another object of the present invention is to allow a user to "zoom in" on an area of a chromatogram or fragmentogram without using a downloaded applet.

A further object of the present invention is to allow a user to "zoom in" on an area of a chromatogram or fragmentogram with two clicks of his mouse, with a process using JavaScript technology coupled with a back-end server application.

A still further object of the present invention is to allow a user to retrieve a list of available ions and select one or more for processing and display.

Another object of the present invention is to allow a user to access GC and GC-MS data residing on a server via the Internet, dynamically re-create the chromatograms and fragmentograms from processed data, and display and change attributes of the resulting images.

DETAILED DESCRIPTION OF THE PREFERRED EMBODIMENT

In the embodiment described herein, the user can be coupled over a network's setting or can access the server remotely via an Internet connection. In both cases, the connection operates using Hypertext Transfer Protocol (HTTP).

Figure 1:
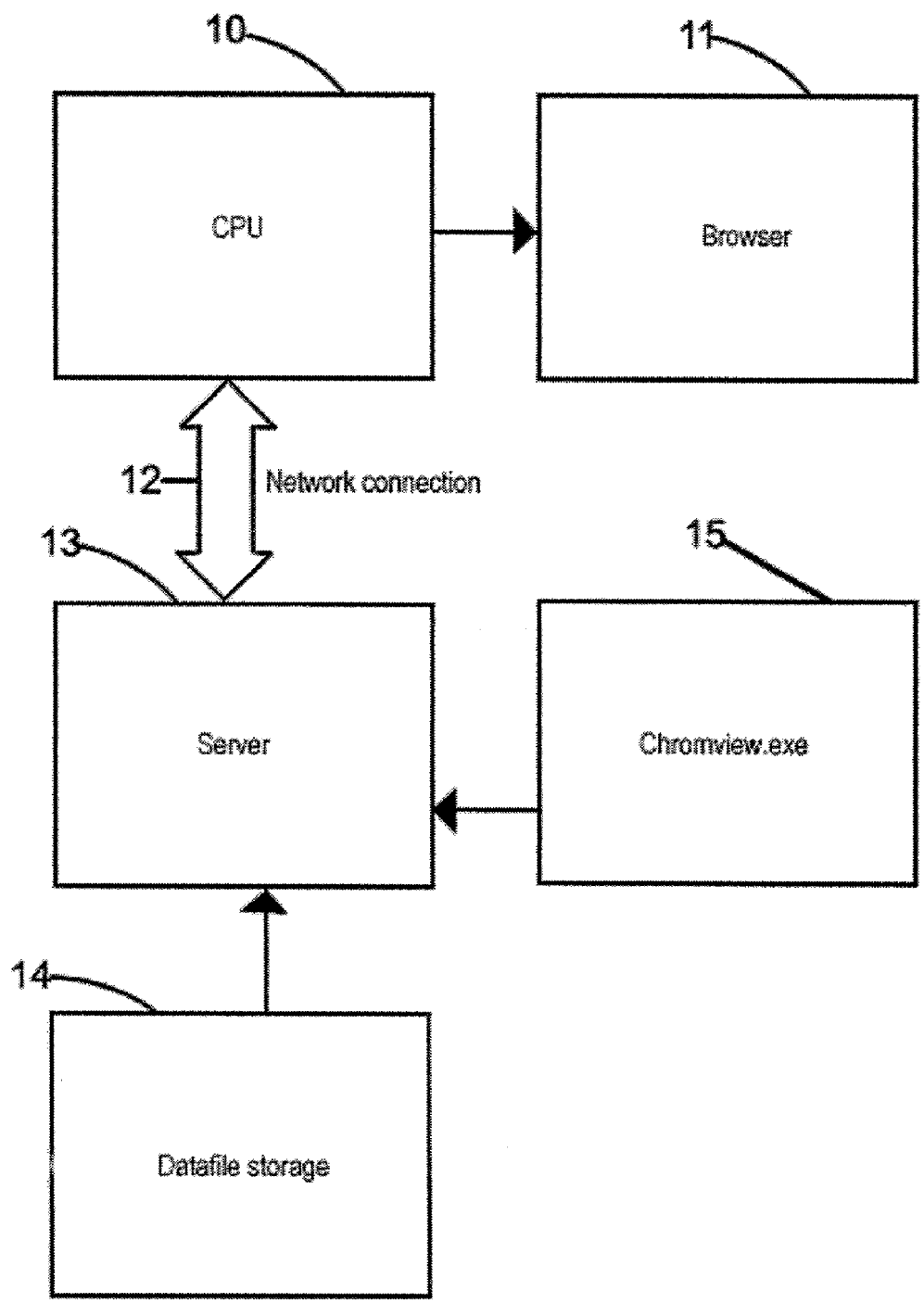
FIG. 1 depicts a simplified block diagram of the components suitable for practicing a preferred embodiment of the present invention.

As shown in FIG. 1, a scientist can "use" the peak viewing program of the present invention by operating a client computer 10 to open a website with the browser 11; he clicks on a link to send information over the network connection 12 to the server 13 using Hypertext Markup Language (HTML). The information, which is processed using Visual Basic and Active Server Pages, relates to GC and GC-MS data in the datafile storage 14. The server 13 uses Chromview.exe 15 to generate a metafile of the selected datafile, then MetaConverts converts the metafile to a .PNG file, then a Chromview and MetaConverter generate a larger image of the file over the browser 11, along with other information. Since Chromview and MetaConverter (hereinafter simply referred to as Chromview) operate on the server 13, the user does not need to download or operate any software.

Figure 2:
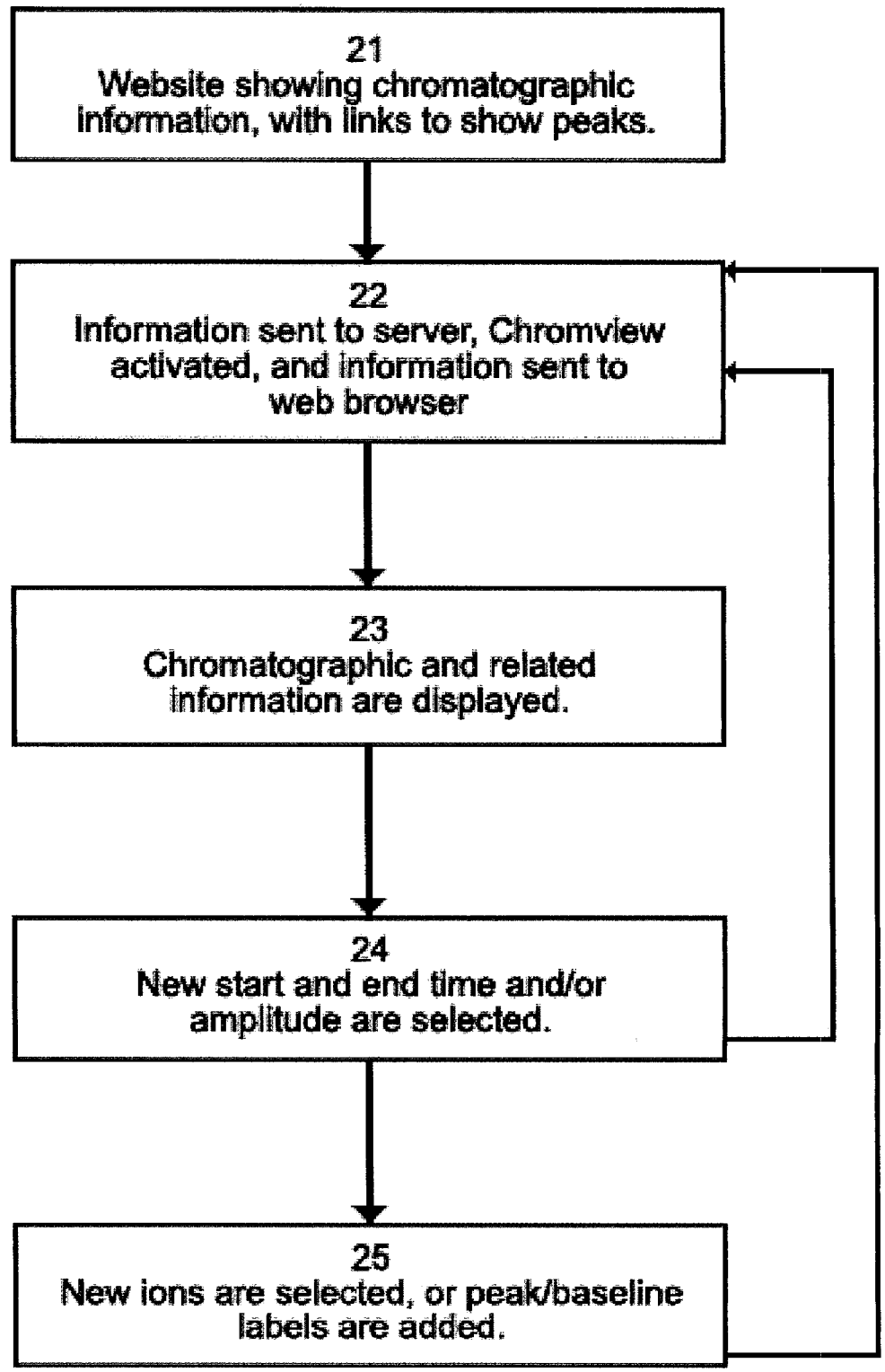
FIG. 2 is a flowchart diagram illustrating the process steps of the present invention.

As the flowchart of FIG. 2 shows, at 21, the browser opens a website showing chromatographic information of interest to the user. Links on the page are associated with the peaks of different chromatograms in the datafile. The user clicks on a list, and, at 22, information is sent to the server and processed suing Visual Basic and Active Server Pages. Chromview is activated and, at 23, chromatographic peaks and related information are sent to the website and displayed to the user. At 24, the user may select new start/end times and/or amplitudes for the peaks. That information, again at 22, is sent to the server and processed, Chromview is activated, and, at 23, new chromatographic peaks and related information are displayed to the user. At 25, when GC-MS data is sought, one or more ions may be selected for viewing, or peak/baseline labels may be added for either GC or GC-MS data, and, at 22, the information is sent to the server 13 and processed, Chromview is activated, and, at 23, new chromatographic peaks and related information are displayed to the user.

Figure 3:
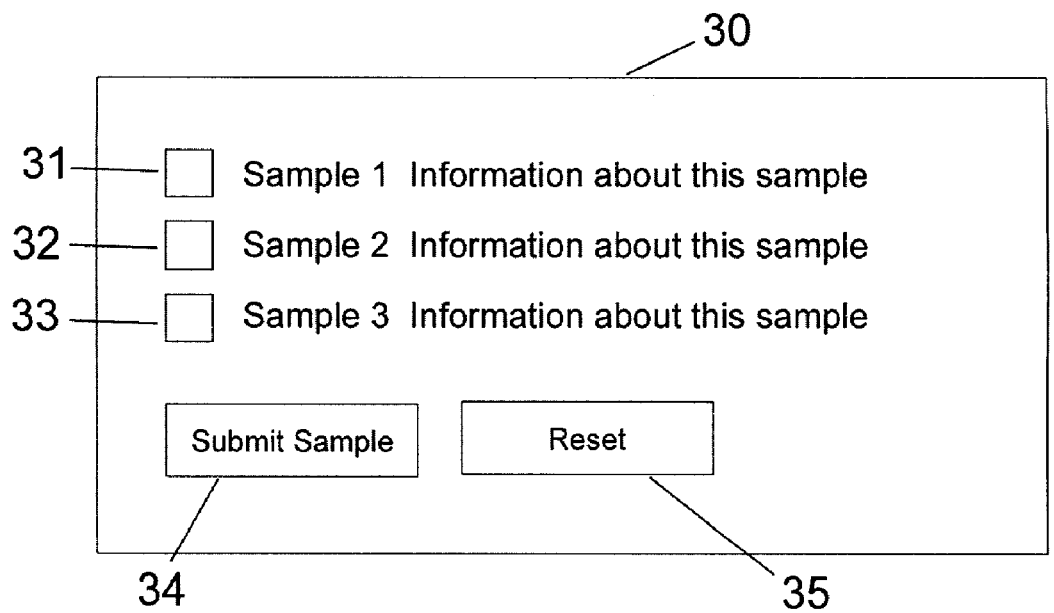
FIG. 3 is a representation of a page displaying a list of samples a geochemist may use for selecting data.

Shown in FIG. 3 is a sample list 30 produced by an application used to acquire data so that a datafile can be identified and retrieved by the peak viewing program. The list allows a user to select from available samples 31, 32, 33 by clicking on any of them and selecting the submit sample button 34, which sends the request to the server and saves it in a session variable. The sample is linked to a database and, if datafile information is available for the sample, that information can be retrieved and used to send the datafile information to the peak viewing program. The reset button 35 allows a user to reset the window.

Figure 4:
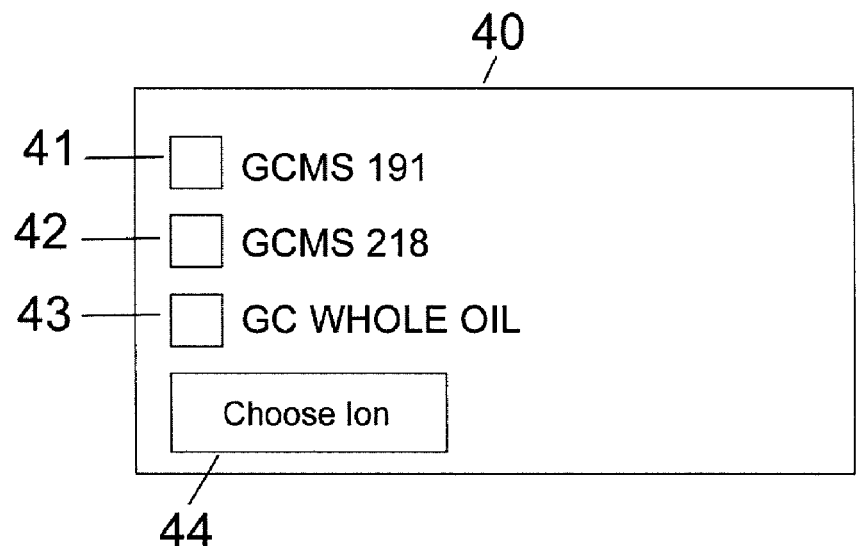
FIG. 4 is a representation of a page displaying a list of data types for which datafiles are available.

Shown in FIG. 4 is a list 40 of different available traces 41, 42, 43. The user can click on one or more of them and then click on the choose ion button 44 in order to see a thumbnail of the related datafiles (see FIG. 5, infra). When the choose ion button 44 is activated, the information regarding the related datafile is sent through a network connection to the server, where the application Chromview generates a small .PNG file of that trace. The .PNG file is then displayed in a list of .PNG files (if more than one is selected) or by itself.

Figure 5:
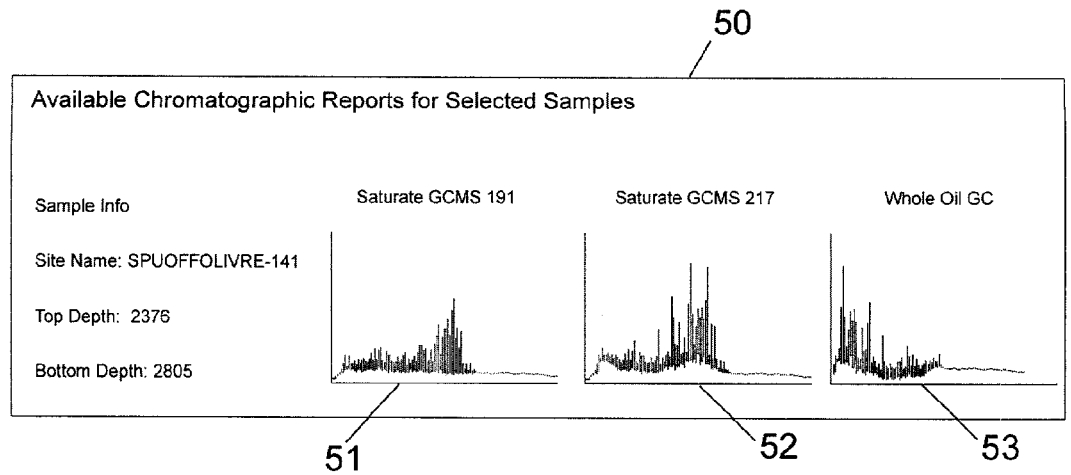
FIG. 5 is a representation of a page displaying a list of thumbnail .PNG files showing images or ions a user can select to view using the present invention.

FIG. 5 shows a list 50 of thumbnail .PNG files with the images of ions 51, 52, 53 a user may wish to view in a larger .PNG format using the peak viewing program. These images of ions 51, 52, 53 were generated by the user's actions described above; in this instance, the user chose to view all three of the ions listed in list 40 in FIG. 4, supra. The image of each of the ions 51, 52, 53 is linked to the name and path of the related datafile, each of which is hosted on the server, which is on the same network as the web server hosting the peak viewing program. Each thumbnail .PNG file acts as a hyperlink to the peak viewing program site. Included in the hyperlink is the path of the datafile. When a hyperlink is clicked, the browser window is redirected to the peak viewing program and the datafile information is retrieved, using a server side script that retrieves the name of the path and maps it accordingly. A large .PNG file is then generated, and the peak viewing program application is launched.

Figure 6:
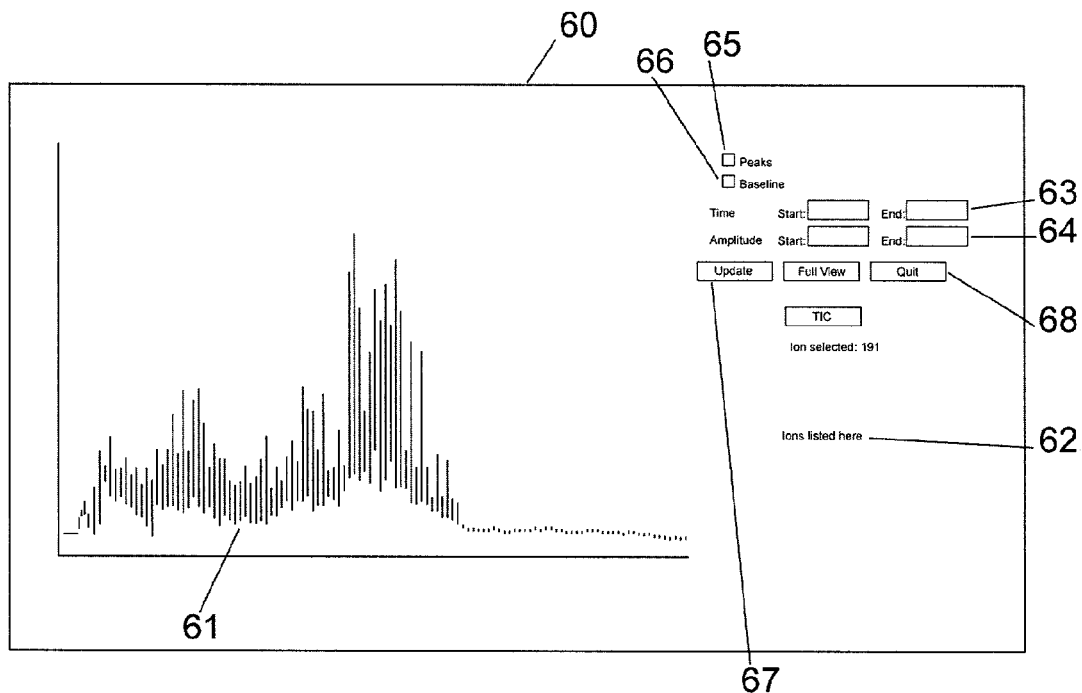
FIG. 6 is a representation of a page displaying a chromatogram trace of an ion, the PNG image of which was generated from the datafile.

FIG. 6 shows a base example of an image 60 produced by the peak viewing program application. The trace 61 shown is a .PNG image of an ion that has been generated from the datafile or series of datafiles. The datafile is found on a network server within the same network as the peak viewing program application. (It does not have to be on the same server, merely on the same network.) As soon as the datafile is retrieved, Chromview processes it and uses it to generate a .PNG file. By default, the .PNG image it generates is called a Total Ion Count (a TIC). There may be many ions for this sample which are available for viewing using the peak viewing program. If so, an ion list 62 appears in the space on the right side of the image 60. Each ion is a hyperlink (created on the server using ASP and set to the user's browser and generated as HTML). By clicking on the link, the process that generated the TIC will repeat itself to generate the appropriate image for that ion (see discussion in FIG. 7, infra). Above the ion list 62 is a time start and end 63 (retention time) and an amplitude start and end 64. The TIC image by default appears with the maximum time and amplitude displayed, and with no peaks or baselines. If the user wishes to see a set of start and end points different than the maximum, he can click on the desired points on the .PNG image (see FIG. 9, infra) or he may select the text value for them and type in his own desired values in the boxes on line 63 or line 64. The process used to generate the .PNG file is repeated, and the new image appears in the left half of the image 60 (see FIG. 10, infra).

On the upper right of the image 60 is a peak label checkbox 65 and a baseline checkbox 66. By default, neither checkbox 65, 66 is checked. However, if a user chooses to check either check box 65, 66, he then clicks the update button 67, which is generated by HTML. A .PNG file is generated as described in FIG. 8, infra.

Clicking the quit button 68 exists the peak viewing program and closes the browser window. All the files created are dynamic and are deleted.

In any of the examples described supra, the user could be performing these tasks remotely or within a network connection. However, the server with the peak viewing program application and the datafiles must be on the same network.

Figure 7:
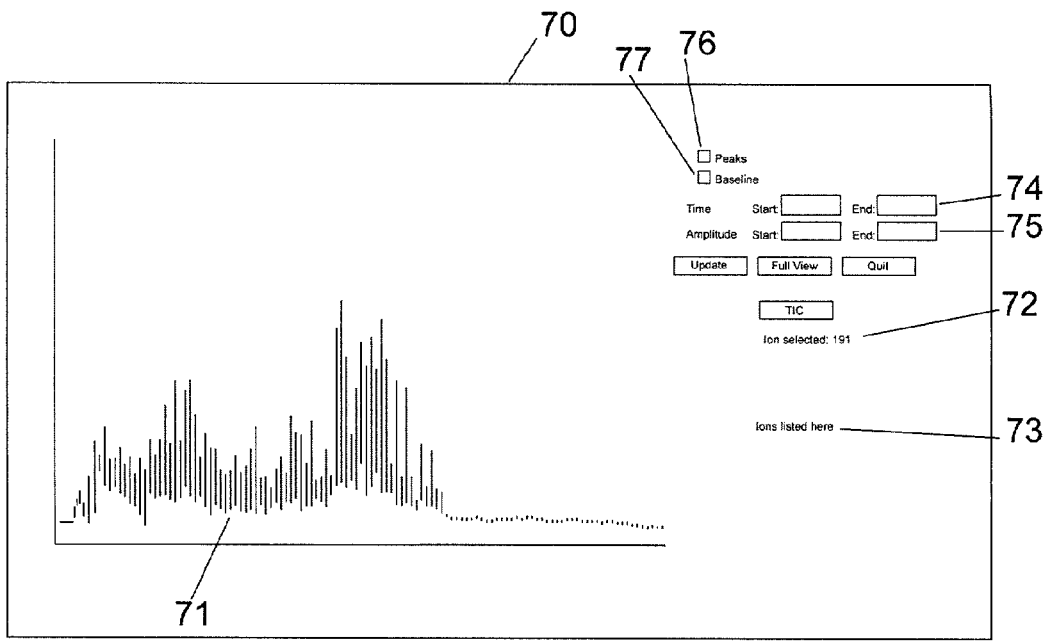
FIG. 7 is a representation of a page displaying a picture of a 191 ion trace.

FIG. 7 shows an image 70 of a 191-ion 71, which was selected for viewing by the user in FIG. 6, supra. The name of the ion 72 is listed above the list 73 of available ions. Any other ion may be selected in a similar manner. In any event, the maximum amplitude and start and end times are plotted out in the .PNG files. As described in FIG. 6 supra, the start and end times 74 and the amplitude 75 may be changed by clicking on the opposite corners of the area to be enlarged, or by changing the values in the start and end text boxes 74 or the amplitude boxes 75. Similarly, peaks and baselines can be added by checking the peak box 76, or the baseline box 77.

Figure 8:
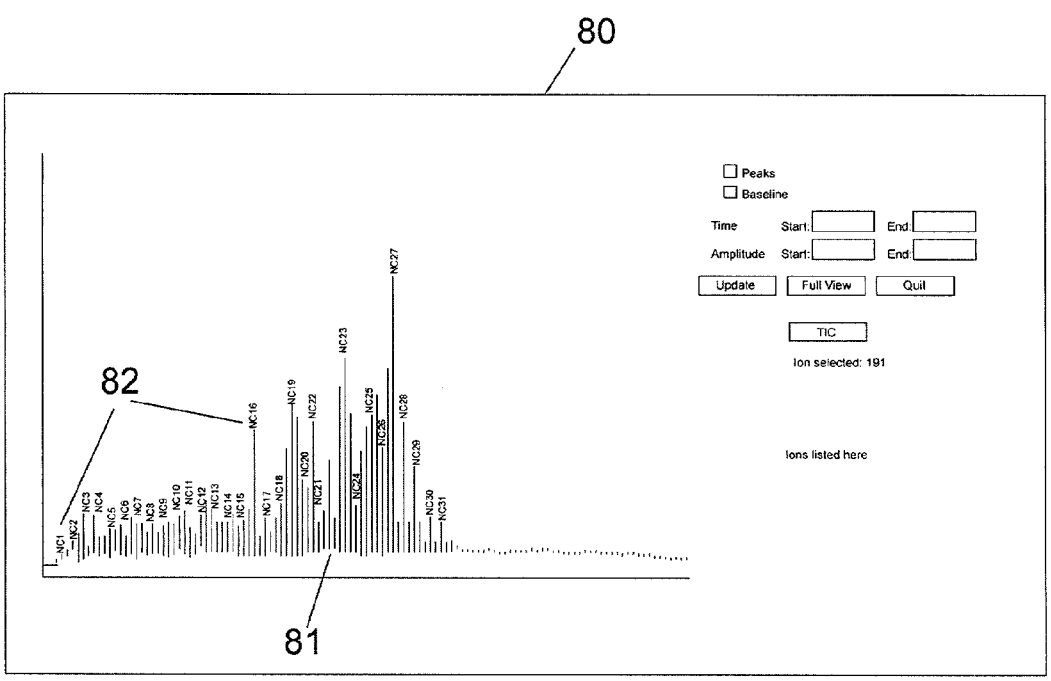
FIG. 8 is a representation of a page displaying the picture generated by use of peak and baseline labels.

FIG. 8 shows an image 80 of a chromatogram trace 81 with peak and baseline labels 82 displayed. This information is contained within the datafiles, but is not displayed by default. If the peak box 83 or the baseline box 84 has been checked, and the image updated, the datafile information for the peaks and labels will have been retrieved from the server, and a new .PNG image processed by Chromview. To the user, the same image will appear to remain, with only the labels appearing. A user may select to view only baselines or only peaks. Similarly, values other than defaults may be entered for start and end for amplitude and/or time, in which case the labels will be plotted as well as described.

Figure 9:
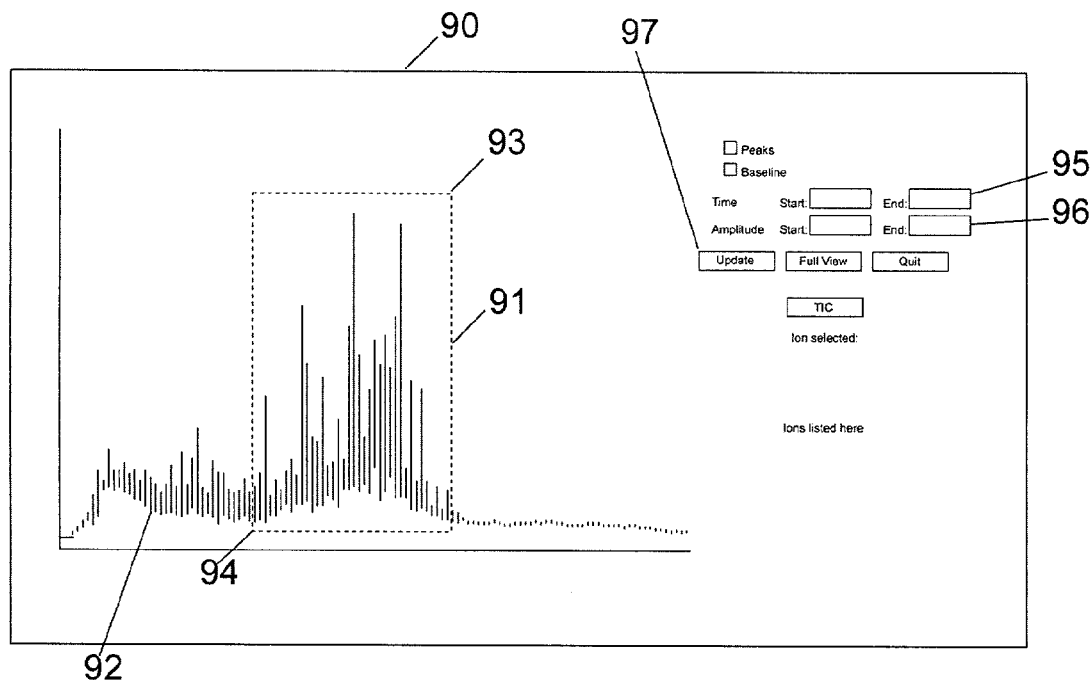
FIG. 9 is a representation of a page displaying a chromatogram trace, the rectangle (in dotted lines) representing the area selected for enlargement.

As shown in the image 90 in FIG. 9, the dotted lines form a rectangle 91 representing an area of a chromatogram trace 92 the user has selected to "zoom in" and enlarge. The process may be done by clicking on opposite corners 93, 94 of the area to be enlarged, or by entering new start and end times 95 or amplitudes 96 in the textboxes, and clicking on the update button 97. The resulting trace is shown in FIG. 10, infra.

Figure 10:
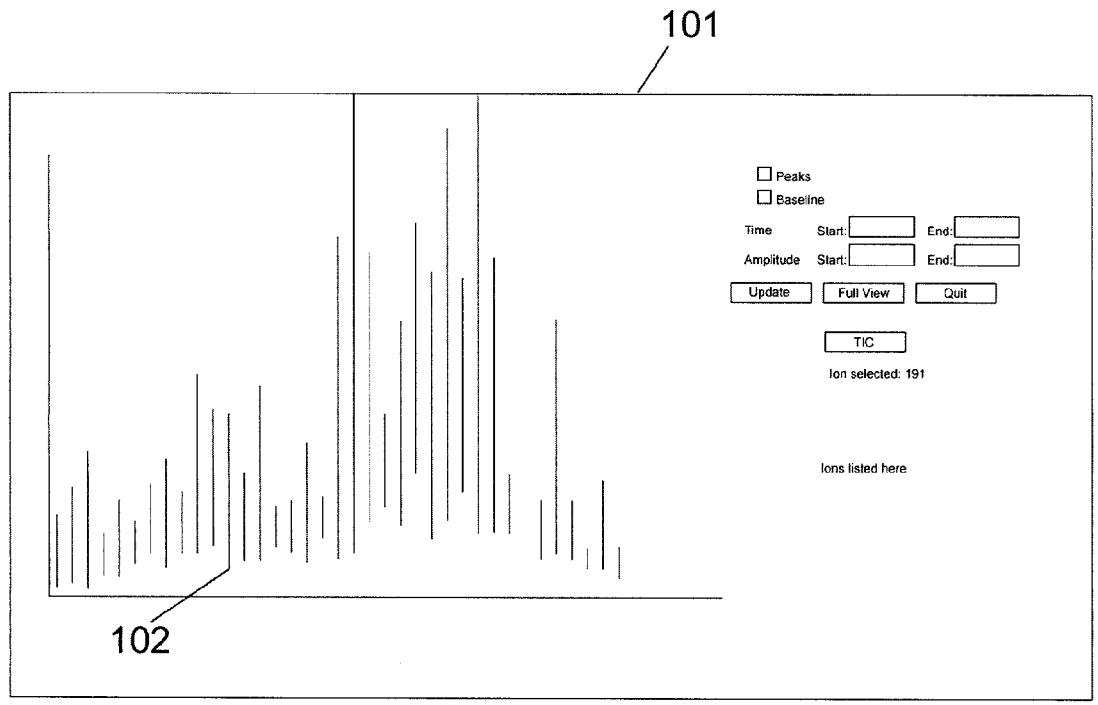
FIG. 10 is a representation of a page displaying the picture generated by the "zoom in" function of the present invention, which has enlarged the rectangular area (in dotted lines) selected in FIG. 9.

As shown in FIG. 10, an image 101 showing an enlarged section of the chromatogram trace 102. A new .PNG image was generated, plotting only the values defined by the user. Peaks and baselines can be added to the image and, unless otherwise specified by the user, the same start and end points will be returned automatically.

We claim:

1. A method for displaying image files of a chromatogram on a computer-implemented screen display, the method comprising the steps of:
    (a) having a user select the chromatogram, the chromatogram having a datafile containing analytical data with optional text files including multiple display parameters;
    (b) using the analytical data in the datafile in generating a metafile of the chromatogram on a server;
    (c) converting the metafile to a first image file;
    (d) sending the first image file to the screen display;
    (e) having the user define an area of the chromatogram;
    (f) using the analytical data in the datafile in generating a replacement metafile containing only the defined area of the chromatogram;
    (g) converting the replacement metafile to a second image file;
    (h) sending the second image file to the screen display and instantaneously replacing the first image file.

2. The method of claim 1 which further comprises:
    (i) having the user select new display parameters from the multiple display parameters included in the optional text files;
    (j) using the analytical data and display parameters in the datafile in generating a second replacement metafile including the new display parameters;
    (k) converting the second replacement metafile to a third image file;
    (l) sending the third image file to the screen display and instantaneously replacing the second image file.

3. The method of claim 2 wherein the display parameters are selected from peak names, retention time labels, baselines, and amplitudes.

4. The method of claim 1 wherein the means of performing step (e) is using a cursor to click on two opposite corners of a rectangular area.

5. The method of claim 1 wherein the server is provided at one location and is in communication with the screen display provided at another location.

6. The method of claim 5 wherein the server is accessible as a web site on an Internet, and the first image file and the second image file are compatible with a web browser, and the screen display is the web browser window.

7. The method of claim 1 wherein the server is a computer running Microsoft Internet Information Server.

8. The method of claim 1 wherein the means for performing steps (b), (c), (f), and (g) are performed by a program running on the server.

9. A method for displaying image files of a GC-MS fragmentogram on a computer implemented screen display, the method comprising the steps of:
    (a) having a user select the fragmentogram, the fragmentogram having a datafile containing analytical data with optional text files including multiple display parameters;
    (b) opening the datafile for the fragmentogram and displaying a list of ion numbers of the fragmentogram;
    (c) having the user select an ion from the list of ion numbers;
    (d) using the analytical data in the datafile in generating a metafile of the ion's fragmentogram on a server;
    (e) converting the metafile to a first image file;
    (f) sending the first image tile to the screen display.

10. The method of claim 9 which further includes the steps of:
    (g) having the user define an area of the ion's fragmentogram;
    (h) using the analytical data in the datafile in generating a replacement metafile containing only the defined area of the fragmentogram;
    (i) converting the replacement metafile to a second image file;
    (j) sending the second image file to the screen display and instantaneously replacing the first image file.

11. The method of claim 10 which further includes the steps of:
    (k) having the user select new display parameters from the multiple display parameters included in the optional text files;
    (l) using the analytical data and display parameters in the datafile in generating a second replacement metafile having the new display parameters;
    (m) converting the second replacement metafile to a third image file;
    (n) sending the third image file to the screen display and instantaneously replacing the second image file.

12. The method of claim 11 wherein the display parameters are selected from peak names, retention time labels, baselines, and amplitudes.

13. The method of claim 10 wherein the means of performing step (g) is using a cursor to click on two opposite corners of a rectangular area.

14. The method of claim 9 wherein the server is provided at one location and is in communication with the screen display provided at another location.

15. The method of claim 14 wherein the server is accessible as a web site on an Internet, and the first image file and the second image file are compatible with a web browser, and the screen display is the web browser window.

16. The method of claim 9 wherein the server is a computer running Microsoft Internet Information Server.

17. The method of claim 9 wherein the means for performing steps (b), (d), and (e) are performed by a program running on the server.

18. The method of claim 1 wherein the means of performing step (e) is entering data into at least one text box on the screen display.

19. The method of claim 10 wherein the means of performing step (g) is entering data into at least one text box on the screen display.

* * * * *